United States Patent
Robinson

(10) Patent No.: US 7,179,602 B2
(45) Date of Patent: Feb. 20, 2007

(54) METHODS FOR SEQUENCING GC-RICH AND CCT REPEAT DNA TEMPLATES

(75) Inventor: Donna L. Robinson, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 10/656,358

(22) Filed: Sep. 4, 2003

(65) Prior Publication Data

US 2005/0053948 A1    Mar. 10, 2005

(51) Int. Cl.
*C13Q 1/68* (2006.01)
*C07H 21/04* (2006.01)
*C12P 19/34* (2006.01)

(52) U.S. Cl. ................ 435/6; 435/91.1; 435/92.1; 536/23.1; 536/24.33

(58) Field of Classification Search ............... 435/174, 435/283.1, 6, 7.1; 422/50, 68.1, 82.05
See application file for complete search history.

(56) References Cited

U.S. PATENT DOCUMENTS

| | | | |
|---|---|---|---|
| 4,965,188 A * | 10/1990 | Mullis et al. | .................. 435/6 |
| 5,075,216 A | 12/1991 | Innis | |
| 5,171,534 A | 12/1992 | Smith | |
| 5,614,365 A | 3/1997 | Tabor | |

OTHER PUBLICATIONS

Product insert/literature: "GC-RICH PCR System", Roche Diagnostics GmbH, No date provided.
Kumari and Anji, 2001, "Sequencing Through GC-rich and AT-rich Sequences with the SequiTherm™ EXCEL™ II DNA Sequencing Kit" Epicentre Technologies technical journal 8(3): 9.
Grunenwald, 2002, "Unlike Other PCR Products, the FailSafe PCR System Amplifies a GC-Rich Template and a 20-Kb Template on the first Try" Epicentre Technologies technical journal 9(3):3.
Sequencing Protocol, Epicentre Technologies, SequiTherm EXCEL™ II DNA Sequencing Kit-LC, for 25-41 cm gels, no date provided.
Sequencing Protocol, Epicentre Technologies, SequiTherm EXCEL™ II DNA Sequencing Kit-LC, for 66 cm gels, no date provided.
Epicentre Technologies, Tech Tips: SequiTherm™ Cycle Sequencing Kit for Manual Sequencing of DNA, no date provided.
Chakrabarti and Schutt, 2001, "The enhancement of PCR amplification by low molecular-weight sulfones" Gene 274:293-298.
Majlingova et al., 2003, "Successful PCR amplification and subcloning of a GC-rich DNA fragment" Qiagen news 1: 18-19.
Web pages concerning DNA Sequencing Trouble-Shooting: Sequencing GC Rich Regions and Hairpins, no date provided.
Product information concerning 7-Deaza-dGTP, Roche Applied Science 2003/2004.
Sanger et al., 1977, Proc. Natl. Acad. Sci. U.S.A., 74: 5463.
Sanger et al., 1980, J. Mol. Biol., 143:161-78.
Schreier et al., 1979, J. Mol. Biol., 129:169-72.
Smith et al., 1985, Nucleic Acids Research, 13:2399-2412.
Smith et al., 1987, Nature, 321:674-79.
Prober et al., 1987, Science, 238:336-41.
1987, Section II, Meth. Enzymol., 155:51-334.
Church et al., 1988, Science, 240:185-88.
Swerdlow et al., 1989, Nucleic Acids Research, 18: 1415-19.
Ruiz-Martinez et al., 1993, Anal. Chem., 2851-58.
Studier, 1989, PNAS, 86:6917-21.
Kieleczawa et al., Science, 258:1787-91; 1992.
Connell et al., 1987, Biotechniques, 5:342-348.
Maxam et al., 1977, Proc. Natl. Acad. Sci. USA, 74:560-564.
Smith et al., 1986, Nature 321:674-679.
Lee et al., 1992, Nucleic Acid Research 20:2471.
Murray, 1989, Nucleic Acids Research 17:8889.
Burgett et al., 1994, In: Automated DNA Sequencing and Analysis, ed. Adams et al., Academic Press, San Diego, CA, pp. 211-215.
Landre et al., 1995, In: PCR Strategies, ed. Innis et al., Academic Press, San Diego, CA, pp. 3-16.
Henke et al., 1997, Nucleic Acids Res. 25:3957-3958.
Baskaran et al., 1996, Genome Res. 6: 633-638.
Innis, 1990, In: PCR Protocols: A Guide to Methods and Applications, ed. Innis et al., Academic Press, San Diego, CA, pp. 54-59.
Fernandez-Rachubinski et al., 1990, DNA Seq. 1: 137-140.
Automated DNA Sequencing, Chemistry Guide (Applied Biosystems Inc., 2000).
Tabor and Richardson, 1995, Proc. Natl. Acad. Sci. USA 92: 6339-6343.
Ewing and Green, 1998, Genome Research 8: 186-194.
Ewing et al., 1998, Genome Research 8: 175-185.

* cited by examiner

*Primary Examiner*—B J Forman
(74) *Attorney, Agent, or Firm*—Kenneth K. Sharples

(57) ABSTRACT

The present invention is directed to a PCR-based method of cycle sequencing DNA and other polynucleotide sequences having high CG content and regions of high GC content, and includes for example DNA strands with a high Cytosine and/or Guanosine content and repeated motifs such as CCT repeats.

10 Claims, 12 Drawing Sheets

[Panel 1 of 1]

[Panel 1 of 1]

[Panel 1 of 2]

[Panel 2 of 2]

[Panel 1 of 2]

[Panel 2 of 2]

[Panel 1 of 2]

[Panel 2 of 2]

[Panel 1 of 2]

[Panel 2 of 2]

[Panel 1 of 1]

[Panel 1 of 1]

METHODS FOR SEQUENCING GC-RICH AND CCT REPEAT DNA TEMPLATES

STATEMENT AS TO RIGHTS TO INVENTIONS MADE UNDER FEDERALLY SPONSORED RESEARCH OR DEVELOPMENT

This invention was made with government support under grant number DE-FG02-98ER62647 from the United States Department of Energy and Contract No. W-7405-ENG-36 awarded by the United States Department of Energy to The Regents of The University of California. The government has certain rights in this invention.

STATEMENT REGARDING COLOR DRAWINGS

This patent or application file contains at least one drawing executed in color. Copies of this patent or patent application publication with color drawings will be provided by the United States Patent and Trademark Office upon request and payment of the necessary fee.

BACKGROUND OF THE INVENTION

The dideoxy chain termination method of sequencing DNA is the basis for most of the DNA sequencing methods employed today, and has widespread use in all automated PCR cycle sequencing methods, instruments and systems (Sanger et al., 1977, Proc. Natl. Acad. Sci U.S.A., 74: 5463). This method relies on gel electrophoresis of a population of variable length single stranded nucleic acid fragments that are generated when oligonucleotide primers hybridized to the target nucleic acid template are extended by the polymerase-driven incorporation of deoxynucleotide triphosphates (dNTPs), and variably terminated by the incorporation of labeled dideoxynucleotide triphosphates (ddNTP). The incorporation of the chain-terminating ddNTPs ideally terminates the extension reaction at all possible base positions, thereby resulting in DNA fragments of all possible lengths, which can then be analyzed electrophoretically to generate a contiguous sequence of bases corresponding to the template.

The chain termination method has been modified in several ways, and serves as the basis for currently available automated DNA sequencing methods. See, e.g., Sanger et al., J. Mol. Biol., 143:161–78 (1980); Schreier et al., J. Mol. Biol., 129:169–72 (1979); Smith et al., Nucleic Acids Research, 13:2399–2412 (1985); Smith et al., Nature, 321: 674–79 (1987), U.S. Pat. No. 5,171,534; Prober et al., Science, 238:33641 (1987); Section II, Meth. Enzymol., 155:51–334 (1987); Church et al., Science, 240:185–88 (1988); Swerdlow et al., Nucleic Acids Research, 18: 1415–19 (1989); Ruiz-Martinez et al., Anal. Chem., 2851–58 (1993); Studier, PNAS, 86:6917–21 (1989); Kieleczawa et. al., Science, 258:1787–91; and Connell et al., Biotechniques, 5:342–348 (1987).

Although the Sanger method was originally performed using radiolabeled fragments which were detected by autoradiography after separation, modern automated DNA sequencers generally are designed for fluorescently labeled fragments, which are detected in real time as they migrate past a detector. Additionally, although the Sanger method was initially conducted with four separate polymerase extension reactions, automated DNA sequencing systems either run these four reactions together or pool separate reactions prior to electrophoresis.

As an example, U.S. Pat. No. 5,171,534 describes a variation of this basic sequencing procedure in which four different fluorescent labels are employed, one for each sequencing reaction. The fragments developed in the A, G, C and T sequencing reactions are then recombined and introduced together onto a separation matrix. A system of optical filters is used to individually detect the fluorophores as they pass the detector. This allows the throughput of a sequencing apparatus to be increased by a factor of four, since the four sequencing reaction which were previously run in four separate lanes or capillaries can now be run in one.

Automated fluorescent DNA sequencing systems utilize either a "dye-primer" method (a variation of the Maxam-Gilbert method (Maxam et al., 1977, Proc. Natl. Acad. Sci. USA, 74:560–564) or a "dye-terminator" method (a variation of the basic Sanger method). The dye-primer method involves the use of a fluorescently-labeled primer in combination with unlabeled ddNTPs. The procedure requires four synthesis reactions and up to four lanes on a gel for each template sequenced (i.e., one lane for each of the base-specific termination products). Following extension of the fluorescently-labeled primer, the sequencing reaction mixtures containing ddNTP termination products are separated electrophoretically. The size-separated, fluorescently-labeled products are automatically scanned with a laser at the bottom of the electrophoretic gel or capillary, and fluorescence is detected with an appropriate monitor (Smith et al., 1986, Nature 321:674–679). In a modification of this method, the primer added to each of the four reactions is labeled with a different fluorescent marker. After the four separate sequencing reactions are completed, the reactions are combined and the mixture is subjected to analysis in a single gel lane or capillary. The different fluorescent labels (one corresponding to each of the four different base-specific termination products) are then individually detected.

The dye-terminator sequencing method utilizes a DNA polymerase to incorporate dNTPs onto the growing end of an unlabeled DNA primer until the enzyme incorporates a chain-terminating, fluorescently-labeled ddNTP (Lee et al., 1992, Nucleic Acid Research 20:2471). The dye-terminator method offers the advantage of not having to synthesize dye-labeled primers. Additionally, each different ddNTP is typically labeled with a different fluorescent marker, permitting all four reactions to be performed simultaneously in a single reaction vessel. This method, for example, is the basis of the various dye-terminator cycle sequencing kits marketed by Applied Biosystems Inc. (Foster City, Calif.).

Automated DNA sequencing methods utilize either dye-primer or dye-terminator methods in combination with thermostable polymerases and PCR cycling (see, e.g., U.S. Pat. No. 5,075,216). Cycle sequencing is a PCR based system involving repeated cycles of heating and cooling, wherein numerous extension products are generated from template DNA by a thermostable polymerase, such as Taq polymerase (Murray, 1989, Nucleic Acids Research 17:8889).

One of the advantages of cycle sequencing is that the high extension temperature discourages the formation of secondary structures on the template. However, certain templates, such as GC-rich sequences, may nevertheless form secondary structures through with DNA polymerases can not read. In dye-terminator sequencing, extension products are labeled only when a dye-labeled dideoxynucleotide terminator is incorporated. If the polymerase falls off the template strand because it has encountered an impassible secondary structure and no dye-labeled terminator is incorporated, the extension fragment created cannot be detected. Similarly, in dye-primer sequencing, if the polymerase dissociates from a partially extended fragment without incorporating a dideoxy terminator, a false stop is generated.

Throughout the scientific literature relating to the sequencing of the human and other genomes, reference is made to extraordinarily difficult and challenging regions for which reliable sequence information could not be obtained. The existence of these regions has impeded the closure of gaps and the final finishing of sequencing projects worldwide, and has fueled the development of a number of improvements in sequencing chemistries, software, and methods aimed at solving the problems presented by these difficult regions. Researchers faced with resolving these difficult regions have applied a variety of techniques, including resequencing, multiplexed PCR, searching for ESTs which overlap contig ends for designing new primers, shatter cloning, and transposon insertion or "bombing" methods.

However, notwithstanding the availability and implementation of these various techniques, the difficulties associated with sequencing certain types of DNA sequences persist. This appears to be especially true for "GC-rich" sequences, for which no universally reliable sequencing solution has emerged. Similarly, certain repeat structures, such as "CCT" repeats continue to confound the available DNA sequencing chemistries. Indeed, the ability to generate sequence data from GC-rich and CCT repeat regions has been an almost insurmountable problem faced by scientists working on the Human Genome Project for years. These GC-rich and CCT repeat regions are also believed to contain coding information crucial to the transcription of genes. Thus, in order to produce accurate and fully finished sequences, new sequencing methods and chemistries are needed to deal with regions that are refractory to standard sequencing methods.

A number of commercially available sequencing chemistries are in widespread use, with those provided by Applied Biosystems Inc. (ABI) being among the most popular. ABI has recently introduced refined DNA sequencing chemistries, such as BigDye® Terminator v. 1.1 and 3.1. To resolve particularly refractory sequence regions, ABI offers a dGTP based sequencing chemistry for use with difficult templates, particularly for templates with high GC content, as well as for templates with certain sequences or patterns. A further enhancement of the dGTP sequencing chemistry utilizes 7-deaza-dGTP. The use of 7-deaza-dGTP is intended to overcome compression problems typically encountered in sequencing GC-rich regions. While these enhanced chemistries represent an improvement over previous systems, they have not been able to produce long, quality read length sequence data in all cases, particularly where GC-rich sequences are involved.

Approaches recommended by automated cycle sequencing kit and instrumentation providers (e.g., Applied Biosystems Inc.) for sequencing GC-rich templates include increasing the DNA denaturing temperature to 98° C.; adding DMSO to the reaction mixture at a concentration of 5%; incubating the reaction mixture at 96° C. for 10 minutes before cycling; adding betaine to a concentration of 1M; doubling reaction components and incubating at 98° C. for 10 minutes before cycling; adding 5–10% formamide or 5–10% glycerol to the reaction mixture; linearizing plasmids before sequencing; shearing the DNA insert into smaller fragments and subcloning; and PCR amplifying the template DNA with the substitution of 7-deaza-dGTP for 75% of the dGTP used in the PCR reaction and then sequencing the PCR product (see, for example, Burgett et al., 1994, In: Automated DNA Sequencing and Analysis, ed. Adams et al., Academic Press, San Diego, Calif., pp. 211–215; Landre et al., 1995, In: PCR Strategies, ed. Innis et al., Academic Press, San Diego, Calif., pp. 3–16; Henke et al., 1997, Nucleic Acids Res. 25:3957–3958; Baskaran et al., 1996, Genome Res. 6: 633–638; Innis, 1990, In: PCR Protocols: A Guide to Methods and Applications, ed. Innis et al., Academic Press, San Diego, Calif., pp. 54–59; Fernandez-Rachubinski et al., 1990, DNA Seq. 1: 137–140).

Different dye-terminator chemistries are also offered for difficult sequences, including GC-rich sequences, and include chemistries which utilize dRhodamine terminators (e.g., dGTP Big Dye kits, Applied Biosystems Inc., Foster City, Calif.). See also, "Automated DNA Sequencing, Chemistry Guide (Applied Biosystems Inc., 2000).

Additionally, a number of thermostable polymerases and mutated thermostable polymerases having better GC-rich template read-through properties have been described. Generally, these polymerases are variants of the well known Taq polymerase. An examples of such a polymerase is the HotStarTaq DNA polymerase marketed by Qiagen (Valencia, Calif.), However, the above methods are frequently not successful, and may also introduce additional problems. For example, where DMSO is added to the reaction mix, too much can impair the performance of the polymerase.

Notwithstanding the development of various sequencing chemistries and systems, there remains a strong need for new sequencing methodologies which are capable of generating reliable sequence data from templates having high GC content, CCT repeat elements, and the like. It would be most desirable for such new sequencing methods to be readily applicable to the now widely used automated cycle sequencing systems.

SUMMARY OF THE INVENTION

The present invention is directed to a PCR-based method of cycle sequencing DNA and other polynucleotide sequences having high CG content and regions of high GC content, and includes for example DNA strands with a high Cytosine and/or Guanosine content and repeated motifs such as CCT repeats. The method of the invention utilizes PCR primers specifically engineered to have higher dissociation temperatures (Td) than those commonly employed in currently available sequencing systems. Such primers may be annealed to the substrate DNA at higher temperatures. The use of higher temperatures during the annealing step of the sequencing process more effectively maintains the template DNA in an open, single-stranded state. Furthermore, higher annealing temperatures inhibit the formation of secondary structural barriers within the primers or on the template DNA, and prevents the formation of reassociated single strand barriers in the template during the primer annealing step.

The resulting preservation of the template's linear single-strand conformation following dissociation of the double strand, permits a thermostable polymerase to then process through the template sequence without encountering barriers to read-through commonly encountered in sequencing GC-rich DNA segments using available systems. A higher temperature during the polymerase extension step is also employed in the method of the invention in order to maintain the "open" conformation state of the DNA being sequenced. The methods of the invention are particularly suited for use with automated cycle sequencing systems, such as the PRISM™ sequencing kits and instrumentation provided by Applied Biosystems Inc.

In one embodiment, the method is applied to fluorescence-based cycle sequencing of a GC-rich sample DNA, briefly as follows. A reaction mixture containing a suitable buffer is prepared. The reaction mixture is provided with a primer set complementary to DNA primer sites flanking or interspersed within the sample DNA, wherein the Td of the primers in the primer set are between about 72° C. and 75° C. Also included in the reaction mixture is a thermostable polymerase, preferably a Taq polymerase or a variant thereof, a mixture of dNTPs and fluorescently-labeled ddNTPs, and the sample DNA. The sequencing reaction first involves dissociating the sample DNA to create single stranded templates, wherein said dissociation is achieved by heating the DNA to between about 92° C. and 95° C. for at least about 3 minutes. The cycle sequencing reaction then begins with annealing the primers to the primer sites, wherein said annealing is achieved at a temperature of between about 65° C. and 67° C. for at least about 30 seconds. Next, the annealed primers are extended by the thermostable polymerase, at a temperature of between about 75° C. and 78° C. for between about 3 to 4 minutes. The reaction mixture is then heated to between about 92° C. and 95° C. in order to dissociate double stranded DNA. The cycle is repeated for a variable number of cycles, typically between about 30 and 60 cycles. The resulting dye-terminated, fluorescently-labeled dideoxynucleic acid fragments are then analyzed to determine the sequence of the sample DNA.

In a particular embodiment, the primers utilized are complementary to a PUC18 vector containing the sample DNA and have the nucleotide sequences shown in Example 1 (i.e., SEQ ID NOS: 1 and 2), primer annealing step is conducted at 67° C. for 30 seconds, and the primer extension step is conducted at 75° C. for 4 minutes.

The method is conveniently applied to automated fluorescence-based cycle sequencing instruments. In a specific embodiment aimed at sequencing GC-rich DNAs, the sequencing reaction is conducted under substantially the following cycle conditions:

Step 1=3 min @ 92° C.
×1 cycle
Step 2=30 sec @ 92° C.
30 sec @ 67° C.
4 min @ 75° C.
×60 cycles
Step 3=soak @ 4° C.

The nucleotide sequence of the sample DNA may then be determined from the fluorescently-labeled ddNTP-terminated DNA fragments created during the sequencing reaction.

In another aspect, a method of sequencing a DNA sample containing CCT repeats on an automated fluorescence-based cycle sequencer is provided. In one embodiment, primers having a Td of between about 57° C. and 75° C. are provided for a dye-terminator sequencing reaction. A reaction mixture is prepared in a suitable buffer, and includes the DNA sample, a Taq polymerase, dNTPs and fluorescently-labeled ddNTPs. The sequencing reaction is conducted under substantially the following cycle conditions:

Step 1=1 min @ 92° C.
×1 cycle
Step 2=15 sec @ 92° C.
10 sec @ 54° C.
4 min @ 65° C.
×60 cycles
Step 3=soak @ 4° C.

The nucleotide sequence of the sample DNA may then be determined from the fluorescently-labeled ddNTP-terminated DNA fragments created during the sequencing reaction.

Also provided are kits for DNA sequencing. In one embodiment, a kit comprises a reaction buffer, high Td primers, dNTPs and fluorescently labeled ddNTPs, and a thermostable DNA polymerase.

BRIEF DESCRIPTION OF THE DRAWINGS

FIG. 1. Comparison of the sequencing method of the invention (A) with modified ABI dGTP sequencing chemistry on a GC-rich template DNA. See Example 2 for further discussion of the results.

FIG. 2. Comparison of the sequencing method of the invention (A) with modified ABI dGTP sequencing chemistry on a GC-rich template DNA. See Example 2 for further discussion of the results.

FIG. 3. Comparison of the sequencing method of the invention (A) with modified ABI dGTP sequencing chemistry on a GC-rich template DNA. See Example 2 for further discussion of the results.

FIG. 4. Comparison of the sequencing method of the invention (A) with modified ABI dGTP sequencing chemistry on a CCT repeat-containing template DNA. See Example 3 for further discussion of the results.

DETAILED DESCRIPTION OF THE INVENTION

Figure 1A:
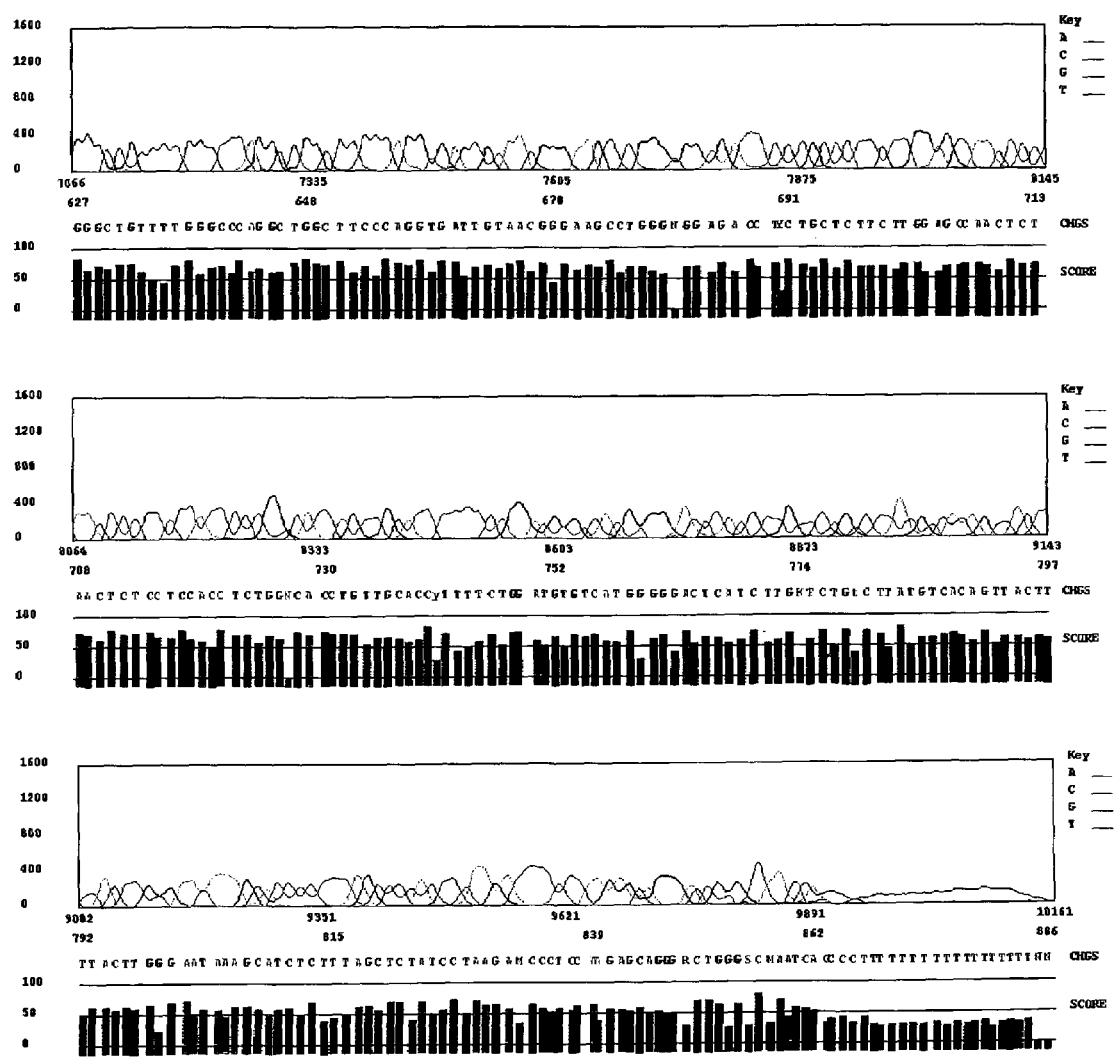
FIGS. 1–4: Fluorogram traces and related data generated from DNA sequencing reactions using (A) the sequencing methods of the invention, compared to (B) modified ABI dGTP sequencing chemistry, on four sample template DNAs. Each figure is composed of a contiguous series of sequence traces, as generated by the ABI Prism Sequencing Analysis Software version 5.0 (Applied Biosystems Inc., Foster City, Calif.). Reaction conditions were as described in Examples 2 and 3. Below the fluorescent trace are two lines of sequence numbering, the second of which corresponds to the extended DNA sequence generated from the template DNA, a line displaying the called nucleotides of the sequenced DNA (directly under the corresponding peak of the trace), and a bar chart indicating the calculated level of confidence for each base call. All sequencing reactions were run on an ABI automated DNA sequencer model 3700.

The invention provides a modified automated cycle DNA sequencing method capable of accurately sequencing DNA characterized by high GC content, regions of high GC content, including those GC-rich regions prone to the formation of template secondary structures or not, and CCT repeats. The application of the method of the invention is further described by way of the Examples, infra. When compared to commercially available chemistries designed specifically for reading through difficult GC-rich or CCT repeat-containing DNA templates, the sequencing method of the invention results in superior read lengths and sequence data.

The method is based on the use of high Td primers in combination with (a) higher annealing temperatures relative to standard PCR sequencing conditions, and (b) higher temperature conditions in the polymerase extension step of the cycle. Optionally, other parameters may also be varied, including without limitation, cycle times and numbers, and concentrations of dNTPs, ddNTPs, primers, polymerase, etc.

The method may be applied to any PCR cycle sequencing technology, such as those commonly employed in automated DNA sequencing. A number of such DNA sequencing platforms are commercially available.

The invention has been successfully applied to the Applied Biosystems automated dye-terminator sequencing system, as described in detail in the Examples which follow. However, it should be understood that the method of the invention may be applied to any automated DNA sequencing system based on PCR-generated extension products incorporating ddNTP terminators, wherein the primers, temperature and time conditions of the cycles, and reagent concentrations may be modified in accordance with the invention. Such systems include without limitation those utilizing dye-terminator chemistry and primer-terminator chemistry.

In addition, the method of the invention may be applied to new DNA sequencing technologies which are also based on polymerase-generated primer extension products, including for example a recently described method termed "pyrosequencing". As disclosed in WO 98/13523, pyrosequencing is based on the detection of inorganic pyrophosphates (PPi) released during a polymerase reaction. As in the Sanger method, a sequencing primer is hybridized to a single stranded DNA template and incubated with a DNA polymerase. In addition to the polymerase, the enzymes ATP sulfurylase, luciferase, and apyrase, and the substrates, adenine 5' phosphosulfate (APS) and luciferin, are added to the reaction. Subsequently, individual nucleotides are added. When the added nucleotide is complementary to the next available base in the template strand, it is incorporated into the extension product, releasing pyrophosphate. In the presence of adenosine 5' phorphosulfate, pyrophosphate is converted into ATP by apryase, in a quantity equimolar to the amount of incorporated nucleotide. The ATP generated by the reaction with apyrase then drives the luciferase-mediated conversion of luciferin to oxyluciferin, generating visible light in amounts that are proportional to the amount of ATP, and thus the number of nucleotides incorporated into the growing DNA template. The light produced by the luciferase-catalyzed reaction is detected by a charge coupled device (CCD) camera.

Definitions

The terms "GC-rich" and "high GC content" are used interchangeably, and as used herein refer to a DNA polymer having a relatively high number of G and/or C bases in its structure, or in a part or region of its structure, relative to the average GC content contained within similar DNAs, genes, or the genomes from which they originate. Generally, DNAs having greater than about 52% GC content are considered GC-rich sequences, with those sequences presenting 70% or more GC content being considered particularly GC-rich and therefore difficult to sequence. Other DNAs containing discrete regions of high GC content may also be considered GC-rich. Some GC-rich regions of DNA form secondary structures, some do not. GC-rich DNAs, templates, or regions thereof are those which are generally refractive to accurate and/or long read length sequencing using available automated cycle sequencing chemistries.

The term "read length" as used herein refers to the number of nucleotides that can be accurately read by an automated sequencing instrument from the set of extension products generated in a cycle sequencing reaction. Read length determinations may be made with the assistance of a software program accompanying or used in conjunction with such automated sequencing instruments. Such software programs may incorporate variable criteria for determining quality read lengths, including for example, the extent to which sequence data meets a level of confidence or similar statistical parameter. Generally, very high quality DNA sequence data will achieve an overall confidence level of greater than 99%.

The term "oligonucleotide" as used herein refers to a polymer of two or more, and typically more than ten, deoxyribonucleotides or ribonucleotides. Oligonucleotides may be prepared by any number of methods known in the art, such as cloning and restriction methods, and direct chemical synthesis methods (e.g., phosphotriester method of Narang et al., 1979, Meth. Enzymol. 68:90–99; phosphodiester method of Brown et al., 1979, Meth. Enzymol. 68:109–151; diethylphosphoramidite method of Beaucage et al., 1981, Tetrahedron Lett. 22:1859–1862; triester method of Matteucci et al., 1981, J. Am. Chem. Soc. 103:3185–3191. Automated synthesis is also routinely employed in the generation of oligonucleotides.

The term "primer" as used herein refers to an oligonucleotide, whether natural or synthetic, which is capable of acting as a point of initiation of DNA synthesis when placed under conditions in which primer extension is initiated. A primer is preferably a single-stranded oligodeoxyribonucleotide. The appropriate length of a primer depends on the intended use of the primer but typically ranges from 15 to 35 nucleotides. A primer need not be fully complementary to the sequence of the template but must be sufficiently complementary to hybridize with a template for primer extension to occur. Various detectable labels may be incorporated into a primer, including, for example, fluorescent dyes, enzymes, biotin, radionuclides, electron dense reagents, haptens, and proteins. Such labels include those which are detectable spectroscopically, photochemically, biochemically, immunochemically, or chemically.

The term "dissociation temperature" (abbreviated as "Td") as used herein refers to the temperature at which a polynucleotide, oligonucleotide or primer will become functionally dissociated from a complementary strand to which it is or may be bound or annealed. The Td of a particular polynucleotide molecule may be calculated using methods known in the art, various software programs which calculate Td, or it may be estimated using the following formula.

$$Td = (\text{number of } A+T \text{ bases}) \times 2° \text{ C.} + (\text{number of } G+C \text{ bases}) \times 4° \text{ C.}$$

The Td of a primer is an important functional characteristic which will influence the conditions under which specific primer annealing to a template DNA can occur. For example, a primer with a high Td will specifically anneal to a complementary sequence on the target DNA (i.e., the priming site) at a higher reaction temperature than one with a lower Td.

The term "melting temperature" as used herein refers to the temperature required to break the hydrogen bonds between complementary polynucleotide strands, thus separating one strand from the other. When used in connection with oligonucleotides or primers, Tm refers to the temperature at which the oligonucleotide or primer is functionally dissociated from the complementary strand to which it is bound.

The term "thermostable polymerase," refers to a DNA polymerase enzyme which is stably heat resistant, retains sufficient activity to effect subsequent primer extension reactions and does not become irreversibly denatured (inactivated) when subjected to elevated temperatures for the time necessary to effect denaturation of double-stranded nucleic acids. As used herein, a thermostable polymerase is suitable for use in a temperature cycling reaction such as the polymerase chain reaction and cycle sequencing reactions. Such thermostable polymerases may include a reverse transcriptase RNA polymerase activity. A number of thermostable polymerases are in widespread use for conducting PCR and PCR-based sequencing reactions. Some of the most widely used thermostable polymerases include the Taq polymerase isolated from Thermus aquaticus. A number of Taq polymerase variants have also been described, some of which are particularly useful in automated DNA sequencing reactions. For example, the "AmpliTaq® DNA polymerase, FS" marketed by ABI for use in ABI's Prism cycle sequencing kits, is a mutant Taq polymerase containing a point mutation in the active site, replacing phenylalanine with tyrosine at residue 667 (F667Y). This mutation results in less discrimination against dideoxynucleotides and results in a more even peak intensity pattern (Tabor and Richardson, 1995, Proc. Natl. Acad. Sci. USA 92: 6339–6343).

Widely available DNA sequencing chemistries utilize both naturally occurring and modified nucleotides. The term "conventional" or "natural" when referring to nucleic acid bases, nucleoside triphosphates, or nucleotides, refers to those which occur naturally (i.e., for DNA these are dATP, dGTP, dCTP and dTTP). Additionally, dITP, and 7-deaza-dGTP are utilized in place of dGTP, and 7deaza-dATP is utilized in place of dATP, in automated DNA sequencing reactions. Collectively these may be referred to as dNTPs.

The term "unconventional" or "modified" when referring to a nucleic acid base, nucleoside, or nucleotide, refers to modifications, derivations, or analogues of conventional bases, nucleosides, or nucleotides. For example, the deoxyribonucleotide form of uracil is an unconventional base in DNA (dUMP), whereas the ribonucleotide form of uracil is a conventional base in RNA (UMP). Unconventional nucleotides include but are not limited to compounds used as terminators for nucleic acid sequencing. Terminator compounds include but are not limited to those compounds which have a 2',3' dideoxy structure and are referred to as dideoxynucleoside triphosphates. The dideoxynucleoside triphosphates ddATP, ddTTP, ddCTP and ddGTP are referred to collectively as ddNTPs. Other unconventional nucleotides include phosphorothioate dNTPs, borano-dNTPs, methyl-phosphonate dNTPs, and ribonucleotide triphosphates (rNTPs). Unconventional bases may be labeled with radioactive isotopes such as $^{32}P$ or $^{35}S$, fluorescent labels, chemiluminescent labels, bioluminescent labels, hapten labels such as biotin, and enzyme labels such as streptavidin or avidin.

The term "cycle sequencing" as used herein refers to a method of sequencing polynucleotides in which successive rounds of denaturation, annealing, and primer extension by a thermostable polymerase in a thermal cycler result in linear amplification of extension products, which are then analyzed via gel or capillary electrophoresis.

Fluorescent labels may include dyes that are negatively charged (i.e., fluorescein family dyes), neutral in charge (i.e., rhodamine family dyes), or positively charged (i.e., cyanine family dyes). Dyes of the fluorescein family include e.g., FAM, HEX, TET, JOE, NAN and ZOE. Dyes of the rhodamine family include Texas Red, ROX, R110, R6G, and TAMRA. FAM, HEX, TET, JOE, NAN, ZOE, ROX, R110, R6G, and TAMRA. These dyes are in widespread use and may be obtained commercially from a number of suppliers, including Perkin-Elmer, Applied Biosystems, and Molecular Probes. Dyes of the cyanine family include Cy2, Cy3, Cy5, and Cy7 and are available through Amersham. For example, DNA sequencing instruments marketed by Applied Biosystems detect fluorescence from four different dyes that are used to identify the A, C, G, and T extension reactions. Each dye emits light at a different wavelength when excited by an argon ion laser. All four colors, and thus all four bases, can be detected and distinguished in a single gel lane or capillary.

Primer Design

The design of primers utilized in DNA cycle sequencing reactions is an important factor in obtaining reliable DNA sequence information. The choice of primer sequences, methods of synthesizing primers, and primer purification choices can impact the quality of DNA sequence information generated in automated cycle sequencing reactions.

In general, there are a number of factors that should be considered in the design of primers used for cycle sequencing reactions. For example, primers should generally be between 15 and 30 bases long, preferably at least about 18 bases long, in order to be capable of achieving stable hybridization to the target template DNA while minimizing the potential for secondary hybridization to non-target sites. In one embodiment, primers are between about 18 and 26 bases in length. Additionally, primers should be designed so as to avoid the possibility of intra or inter primer hybridization, which may result in the formation of primer dimers or primer oligomers. The potential formation of secondary structures within a primer should be minimized. Palindromic sequences, therefore, should generally be avoided as these sequences tend to form stable secondary structures which preclude good hybridization to the template strand. Typically, stretches of identical bases should also be avoided.

With respect to the template DNA, primers should be selected for their ability to stably hybridize to the target region of the template, and thus selection of a suitable target region, to which a good primer may be designed, should be taken into consideration. In this regard, generally, primers should not be designed to anneal to regions of secondary structure within the target having a higher melting point than the primer. Non-template, complementary 5' extensions may be added to primers to allow a variety of useful post-amplification manipulations of the PCR product without significant effect on the amplification itself. These 5' extensions can be restriction sites, promoter sequences, etc.

Methods and tools for the design and synthesis of oligonucleotide primers are well known in the art. For example, various software tools are widely available to assist in the design of primers optimized for a particular set of circumstances, including for example, Primer Express™ software (Applied Biosystems, Foster City, Calif.), Primer3 (Whitehead Institute, Cambridge, Mass.), and Consed (David Gordon, Univ. Washington). Typical "primer picking" programs permit variable length and Td parameters, and assist in avoiding the design of primers with palindromic sequences or other potential secondary structure problems, primers with complementarity to non-target regions of the template DNA, etc.

In designing primers for use in the sequencing method of the invention, other factors which should be taken into consideration include the Td of the primer, its length, and its distance from the target sequence.

The Td of a primer suitable for use in the GC-rich DNA sequencing method of the invention should be in the range of approximately 68° C. to 78° C., preferably between 72° C. to 74° C. and more preferably at about 74° C. However, as will be appreciated by those skilled in the art, the Td of a particular primer will depend on the template to be sequenced, including for example, the nature of the vector in which the target DNA resides for sequencing purposes. In one embodiment, described further in the Examples, infra, forward and reverse primers have Tds of about 74° C. and 73° C. respectively (and annealing is conducted at 67° C., optimally).

The following formula may be used to estimate the dissociation temperature (Td) of an oligonucleotide primer:

$$Td = (\text{number of } A+T \text{ bases}) \times 2° \text{ C.} + (\text{number of } G+C \text{ bases}) \times 4° \text{ C.}$$

An example of the design and use of high Td primers is presented in Example 1, infra.

DNA Polymerases

A number of thermostable DNA polymerases are presently utilized in automated cycle sequencing protocols, most of which are variants of the Taq polymerase.

In cycle sequencing reactions, the quantity of the template DNA can be a reaction-limiting factor. This is a result of the linear amplification achieved with chain-termination, contrasted with the exponential amplification achieved where full length templates are amplified, and a result of polymerase discrimination against the incorporation of unconventional nucleotides, such as the ddNTPs used in dye terminator automated sequencing. The use of high concentrations of terminator ddNTPs relative to dNTPs in sequencing reaction mixtures can compensate for this discrimination, thereby driving the reaction to create extension products covering all possible fragment lengths. However, due principally to the high cost of terminator ddNTPs, the ratio of ddNTPs to dNTPs necessary to drive sufficient ddNTP incorporation is generally achieved by using very low concentrations of dNTPs. However, the use of very low dNTP concentrations tends to result in inefficient amplification due to the lack of natural bases required by the polymerase to build extension products.

More recently, a number of new generation thermostable polymerases, having reduced propensities to discriminate against incorporating fluorescently labeled nucleotides into the extension products, have been described. See, for example, European Patent No. 0 655 506 A1; U.S. Pat. No. 5,614,365. One example of a modified thermostable DNA polymerase is the mutated form of *T. aquaticus* DNA polymerase having a tyrosine residue at position 667 (instead of a phenylalanine residue), i.e. the F667Y mutated form of Taq DNA polymerase. For example, AmpliTaq Polymerase FS, manufactured by Roche Diagnostics Corp. (Indianapolis, Ind.) and marketed through Applied Biosystems, Inc. (Foster City, Calif.) is a mutated form of *T. aquaticus* DNA polymerase having the F667Y mutation and an aspartic acid residue at position 46 (instead of a glycine residue; G46D mutation). The F667Y mutation results in less discrimination against dideoxynucleotides and results in a more even peak intensity pattern (Tabor and Richardson, 1995, Proc. Natl. Acad. Sci. USA 92: 6339–6343), thereby effectively reducing the amount of ddNTP required for efficient nucleic acid sequencing of a target by hundreds to thousands-fold.

In one embodiment of the method of the invention, Taq polymerase or mutants thereof are used. In a specific embodiment, AmpliTaq Polymerase FS (Applied Biosystems, Inc., Foster City, Calif.) is employed in the cycle sequencing reaction, preferably using ABI's BigDye Terminator version 3.0 (dGTP) system. Other mutant polymerases may be used in the practice of the method of the invention, provided that they retain enzymatic activity at the high extension temperature ranges utilized in the method, for at least a time sufficient to process through the target template and generate extension products that will provide reliable DNA sequence data. In other embodiments, multiple polymerases may be used in the same sequencing reaction, such as, for example, the combination of polymerases described in U.S. patent application No. 0020177129.

Where the method of the invention is applied to sequencing RNA templates, thermostable polymerases with reverse transcriptase activity are used, including for example MuLV or rTth DNA polymerase. For RNA templates with high GC content or complex secondary structure, the high-temperature reverse transcriptase activity of thermostable rTth DNA Polymerase is preferred.

Preferred embodiments utilize "processive" polymerases with a reduced ddNTP discrimination propensity, i.e., polymerases with higher processivity than wild-type Taq DNA polymerase, an example being AmpliTaq Polymerase FS.

Thermostable polymerase functional stabilities at elevated primer extension reaction temperature conditions will vary from enzyme to enzyme. In defining the optimum temperature for the polymerase extension step of a sequencing reaction involving a high GC template, a series of routine sequencing experiments may be conducted with one or more polymerase enzymes under standard conditions and using variable temperatures and/or primer extension times. For such a study, target DNAs with known high GC content areas may be used to evaluate the conditions under which the polymerase successfully reads through the problem area. Alternatively, any target DNA may be sequenced, wherein the functional temperature and stability characteristics are examined. In this way, the best parameters for a given polymerase may be defined.

In some cases, the upper end of the functional temperature ranges for a commercially-available DNA sequencing polymerases may be increased for variable time periods without losing polymerase function. For example, an analysis of the polymerase in ABI's Big Dye Terminator version 3.0 system revealed that this enzyme retains good functionality for as much as 5.5 hrs at temperatures which exceed the manufacturer's specifications (i.e., 60° C.) by 15–22° C.

Cycle Sequencing Protocols—Dye Terminator Chemistry

Dissociation Conditions

The melting temperatures and other conditions required for achieving the dissociation of two polynucleotide strands are generally well known. Typical DNA cycle sequencing protocols call for a top-level dissociation cycle run at 92–96° C. for between 30 seconds and 5 minutes, depending upon the nature of the template to be sequenced. These conditions will effectively dissociate double stranded DNAs, primers from templates, etc.

In one embodiment of the method of the invention, applied to sequencing GC-rich DNAs, dissociation of double stranded DNA and primer from single stranded template is achieved with a 92° C. cycle lasting approximately 1 to 3 minutes, more preferably between about 2 to 3 minutes, and most preferably for approximately 3 minutes. Higher dissociation temperatures may be used, typically up to about 95 or 96° C., without substantial loss of DNA polymerase activity.

Different thermostable polymerases will have different physical characteristics, including tolerance to high temperatures required for dissociation. Thus, some enzymes may lose activity if subjected to higher dissociation conditions for longer periods of time. The temperature at which effective dissociation is achieved without substantial loss of polymerase activity during the total number of cycles in the sequencing reaction can be determined empirically. One factor that should also be taken into consideration is the time and temperature used for the extension cycle, as higher temperatures at that point of the sequencing reaction will place additional stress on the ability of the polymerase to retain functional enzymatic activity. Where the highest extension temperatures are used, it may be desirable, for example, for the dissociation cycle to be run at a lower dissociation temperature, i.e., 92° C. instead of 95° C.

In a specific embodiment, dissociation of a template containing GC-rich sequence is achieved by heating at 92° C., which results in the dissociation of any double stranded DNA template and the dissociation of any secondary structural elements in single stranded templates. Typically, 3 minutes is sufficient to achieve complete dissociation for such DNA templates. Following this initial denaturation, a cycle condition of 92° C. for approximately 30 seconds begins the PCR sequencing cycle. Following this, the cycle is completed with a primer annealing step followed by a polymerase extension step, as further described below. The reaction is then run through the same cycle of dissociation, primer annealing, and extension, for a number of cycles, typically between about 30 and 70 cycles, more typically between about 40 and 60 cycles, before the reaction is stopped by cooling the reaction mixture, typically to between about 3° C. and 6° C. In a particular embodiment exemplified herein (see Example 2), 60 cycles are used and the reaction is terminated by cooling the reaction mixture to 4° C.

Another embodiment relates to sequencing DNAs containing CCT repeat elements. When sequencing such DNAs, denaturation may be achieved, for example, at 92° C. for approximately 1 to 3 minutes, preferably for 1 minute.

Annealing Conditions

In the practice of the method of the invention, an annealing step at higher temperatures compared to convention cycling conditions is employed to retain the dissociated condition of the template DNA following the denaturation step. The precise annealing temperature employed for a given template will depend on the Td for the primers used in the reaction. Typically, the annealing temperature should be between 3 and 10° C. below the calculated Td of the primer utilized, preferably between 5 and 7° C. below the primer Td. Optimal annealing temperatures may be determined empirically by conducting sequencing runs on a common template, using the same primers, at variable annealing temperatures. Testing various annealing conditions on multiple templates using primers with high Tds (74.2° C. and 73.4° C.) revealed that annealing temperatures between 64° C. and 67° C. resulted in successful reads through high GC content regions. Substantially better results were obtained with annealing temperatures between 66° C. and 67° C., and the best results were obtained at 67° C.

Annealing times may vary, and optimal annealing times may also be determined empirically. In general, annealing times should fall within the range of about 10 and 60 seconds, more preferably between about 30 and 45 seconds, and most preferably at about 30 seconds.

In one embodiment, sequencing a GC-rich template utilizes cycle conditions which incorporate a 30 second, 67OC anneal cycle. This combination of temperature and time proved optimal for a number of high GC content templates that were evaluated experimentally.

In another embodiment, for sequencing DNAs containing CCT repeats, annealing is conducted at a lower temparature, typically at about 54° C. for between 10 and 30 seconds. In a specific embodiment, annealing is conducted at 54° C. for 10 seconds. This combination of temperature and time proved optimal for sequencing templates containing CCT repetitive elements.

Extension Conditions

Optimal extension conditions will vary, depending on the precise sequence of the template, the primers being utilized, etc. In general, the method of the invention is successful at reading through high GC content templates where extension temperatures are between 70° C. and 82° C. In one embodiment, the extension step is carried out at between 75° C. and 78° C. for about 3 to 4 minutes. In a specific embodiment applied to sequencing GC-rich DNA, the extension step in the cycle is run at 75° C. for about 4 minutes.

When the method of the invention is applied to sequencing DNAs containing CCT repeat elements, the extension temperature is held at between about 65–67° C. for between about 3 and 4 minutes. In a specific embodiment applied to sequencing CCT repeat containing DNA, the extension step is run at 65° C. for about 4 minutes.

Other Cycling Conditions and Reaction Parameters

As will be appreciated by those skilled in DNA sequencing, a number of other parameters involved in the sequencing reaction may be varied to achieve various objectives, including for example, increasing the number of cycles, varying the concentration of the reactants, etc.

In one embodiment, applied to sequencing both GC-rich and CCT repeat containing DNA, the concentration of thermostable polymerase (i.e., AmpliTaq Polymerase FS) is increased in the sequencing reaction mixture in order to increase the level of enzymatic activity available in the reaction. Optionally, the concentration of fluorescently labeled ddNTPs may also be increased, in order to provide a greater number of terminator bases, thereby increasing the chances of incorporating fluorescent terminators at each cycle. A further enhancement involves reducing the molarity of the primers included in the reaction. It was determined empirically, for example, that lowering the molar concentration of the primers drives the number of incorporated bases in the extension step further. Fewer primer molecules result in the occurrence of fewer primed templates, thereby increasing the number of bases added to the fewer primed templates rather than adding fewer bases to more primed templates. In one embodiment, primer is added to the reaction mixture at a concentration of about 0.33 uM.

The number of thermocycles employed to sequence a particular template may vary, and will depend on factors such as the quantity of template being sequenced, its purity, etc. In general, between about 30 and 70 cycles are used, more preferably approximately 60 cycles.

Buffer components utilized in sequencing reactions are typically provided in a reaction mixture containing the polymerase, and typically include Tris-HCl, ammonium sulfate, and magnesium chloride. Various buffers suitable for polymerase-driven sequencing reactions are known in the art and may be prepared for use in the practice of the methods of the invention.

Deoxynucleotides added to the sequencing reaction mixture may be selected from dGTP, dATP, dTTP and dCTP, as well as various derivatives thereof capable of being incorporated into an extension product by a thermostable polymerase in a cycle sequencing reaction. Useful deoxynucleotides include thionucleotides, 7-deaza-2'-dGTP, 7-deaza-2'-dATP, deoxyinosine triphosphate (used as a substitute dATP, dGTP, dTTP or dCTP), and the like. Deoxynucleotides and derivatives thereof are generally incorporated into the sequencing reaction at concentrations ranging from 300 µM to 2 mM. The optimal ratio of terminator ddNTPs to dNTPs may vary.

As an example, when sequencing GC-rich or CCT repeat containing DNA using the method of the invention, a reaction mixture may contain the following components:
- 1.0 µl dGTP BDTv3 terminator mixture, containing polymerase, dNTPs and ddNTPs in a buffer (ABI, Foster City, Calif.)
- 0.0 µl water
- 0.31 µl primer from 6.4 µM stock, yielding a final concentration of 0.48 µl
- 1.0 µl halfTERM buffer
- 3.0 µl template DNA from 35 ng/ml stock The method of the invention may conveniently utilize the premixed reaction components provided with commercially available sequencing kits. In one embodiment, the dGTP BDT Version 3.0 reaction mixture from Applied Biosystems Inc. (Foster City, Calif.) is utilized, wherein 1 µl of the mix is diluted to a final reaction volume of 5 µl.

It should be clear to those skilled in the art that conditions within the recommended parameter ranges may be varied to meet the sequencing challenge presented by any given target polynucleotide. Optimization of conditions which yield the best sequencing results may be achieved using a series of variable sequencing runs, on standardized DNAs or on the target DNA or polynucleotide itself.

Sequencing Kits

Another aspect of the invention provides kits for DNA sequencing. In one embodiment, such a kit may comprise a reaction buffer, high Td primers, dNTPs and fluorescently labeled ddNTPs, and a thermostable DNA polymerase. The cycling conditions of the invention may also be included as instructional material, computer software, etc.

EXAMPLES

Example 1

Primer Design and Preparation

Primers having higher Tds were designed to hybridize to the PUC18 plasmid vector in which target DNAs were inserted. Two primer sites on the PUC18 vector that would hybridize primers with an average Td=73.8° C. were located. These primers are up and downstream of the standard M13 forward and reverse primers (respectively) used in sequencing reactions.

The sequences of the primers in this primer set are as follows:

PCU18 Forward Primer:
GC-PUC18 FP=24mer (PUC18 position 327–350) Td=74.2

(SEQ ID NO: 1)
5' GCT GCA AGG CGA TTA AGT TGG GTA 3'

PUC18 Reverse Primer:
GC-PUC18 RP=26mer (starts at position 491–516) Td=73.4

(SEQ ID NO: 2)
5' GTT GTG TGG AAT TGT GAG CGG ATA AC 3'

Both primers were synthesized using a custom MerMade instrument (BioAutomation, Plano, Tex.) and used in the comparative sequencing experiments described in examples 2 and 3, below Example 2

High GC Content Template Sequencing

Materials and Methods

Automated dye-terminator sequencing reactions on several GC-rich template DNAs were conducted using both modified standard sequencing conditions and the GC-rich sequencing method of the invention. An Applied Biosystems model 3700 sequencer was utilized for all sequencing runs.

The reaction mixture was as follows:
- 1.0 µl dGTP BDTv3 terminator mixture, containing polymerase, dNTPs and ddNTPs in a buffer (ABI, Foster City, Calif.)
- 0.0 µl water
- 0.31 µl primer from 6.4 µM stock, yielding a final concentration of 0.48 µl 1.0 µl halfTERM buffer
- 3.0 µl template DNA from 35 ng/ml stock Cycling conditions were as follows:
Step 1=3 min @ 92° C.
  ×1 cycle
Step 2=30 sec @ 92° C.
  30 sec @ 67° C.
  4 min @ 75° C.
  ×60 cycles
Step 3=soak @ 4° C.

Template DNA was prepared using standard techniques and diluted to a final concentration of approximately 33 ng/µl. The primers described in Example 1 were used in the reaction testing the method of the invention, but not in the reaction modified standard sequencing reaction.

Results

The DNA sequencing results obtained using the GC sequencing method of the invention and modified standard sequencing methodology and conditions on the same template DNA were compared. The results are shown in FIGS. 1–3. These figures show panels corresponding to windows in a computer program used in visualizing automated DNA sequence data (ABI Prism Sequencing Analysis Software version 5.0). The series of panels in each figure represents a contiguous DNA sequence within the entire read length obtained for the sequenced template. The numbers shown below the fluorogram traces and immediately above the nucleotide base calls represent the base position in the full length read for a particular sequencing run. However, in some cases, the panels present overlapping bases, such that, for example, the first panel ends in nucleotide residue number 375, and the next panel begins with nucleotide number 368 (see, for example, FIG. 2A, Sheet 1, top two panels).

Figure 1B:
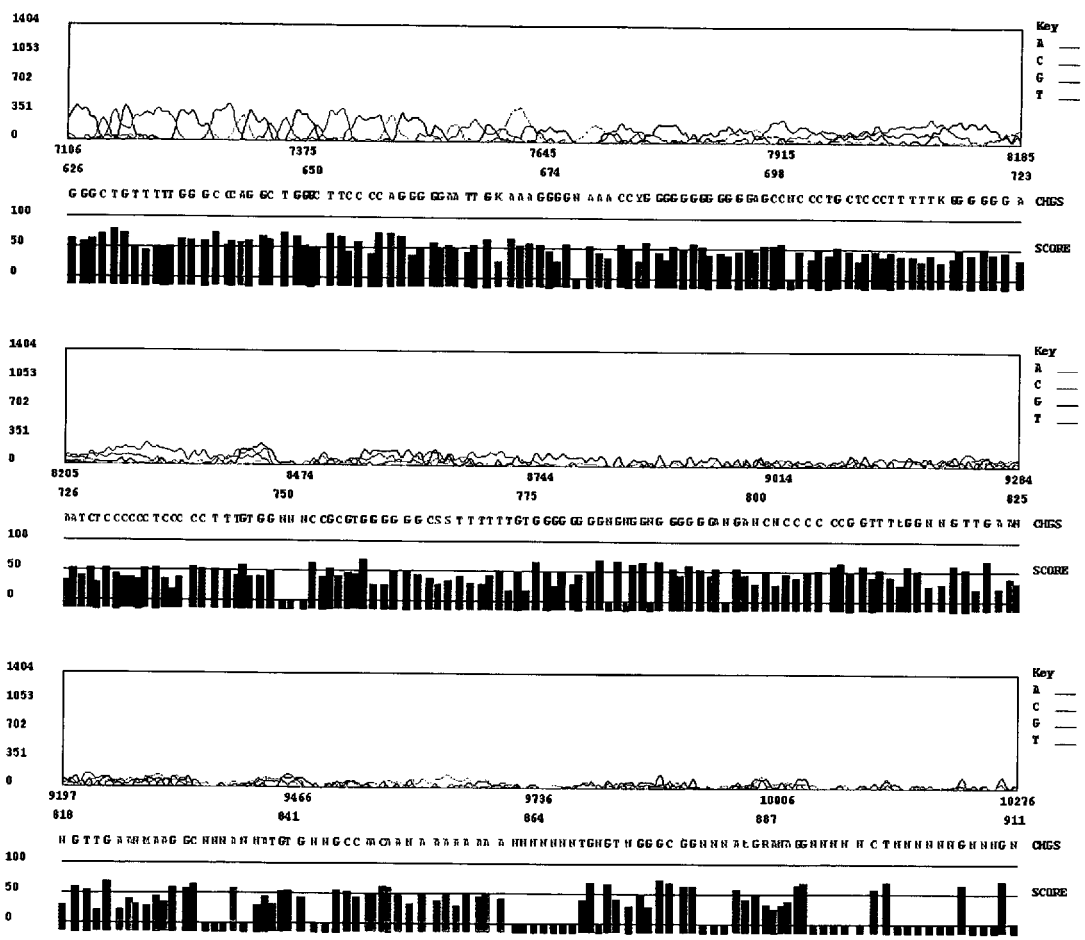

FIGS. 1A and 1B compare sequencing data generated from a high GC content template DNA using two different sequencing protocols in an automated dye-terminator cycle sequencer. FIG. 1A shows the sequence data generated using the method of the invention, i.e., high Td primers and high temperature cycling conditions (see Materials & Methods, supra, for details), across template nucleotide residues 627 to 886. FIG. 1B shows the sequence data generated using standard primers and the high temperature cycling conditions of the invention (see Materials & Methods, supra, for details), across template nucleotide residues 626 to 911. As can be seen from a comparison of the sequence data, the method of the invention was able to generate callable sequence data in this high read length region, approximately up through nucleotide residue 862 (FIG. 1A). In contrast, the modified standard sequencing reaction was unable to generate readable sequence data past approximately nucleotide residue 674 (FIG. 1B). Quality base reads, as determined by the PHRED algorithm, set at 99% confidence level (Ewing and Green, 1998, Genome Research 8: 186–194; Ewing et al., 1998, Genome Research 8: 175–185), were 655 base pairs using the method of the invention, versus 571 using the modified standard conditions. Thus, this example illustrates that the method of the invention successfully read through a difficult GC-rich region and go on to create extension products providing a significantly longer read length.

Figure 2A:
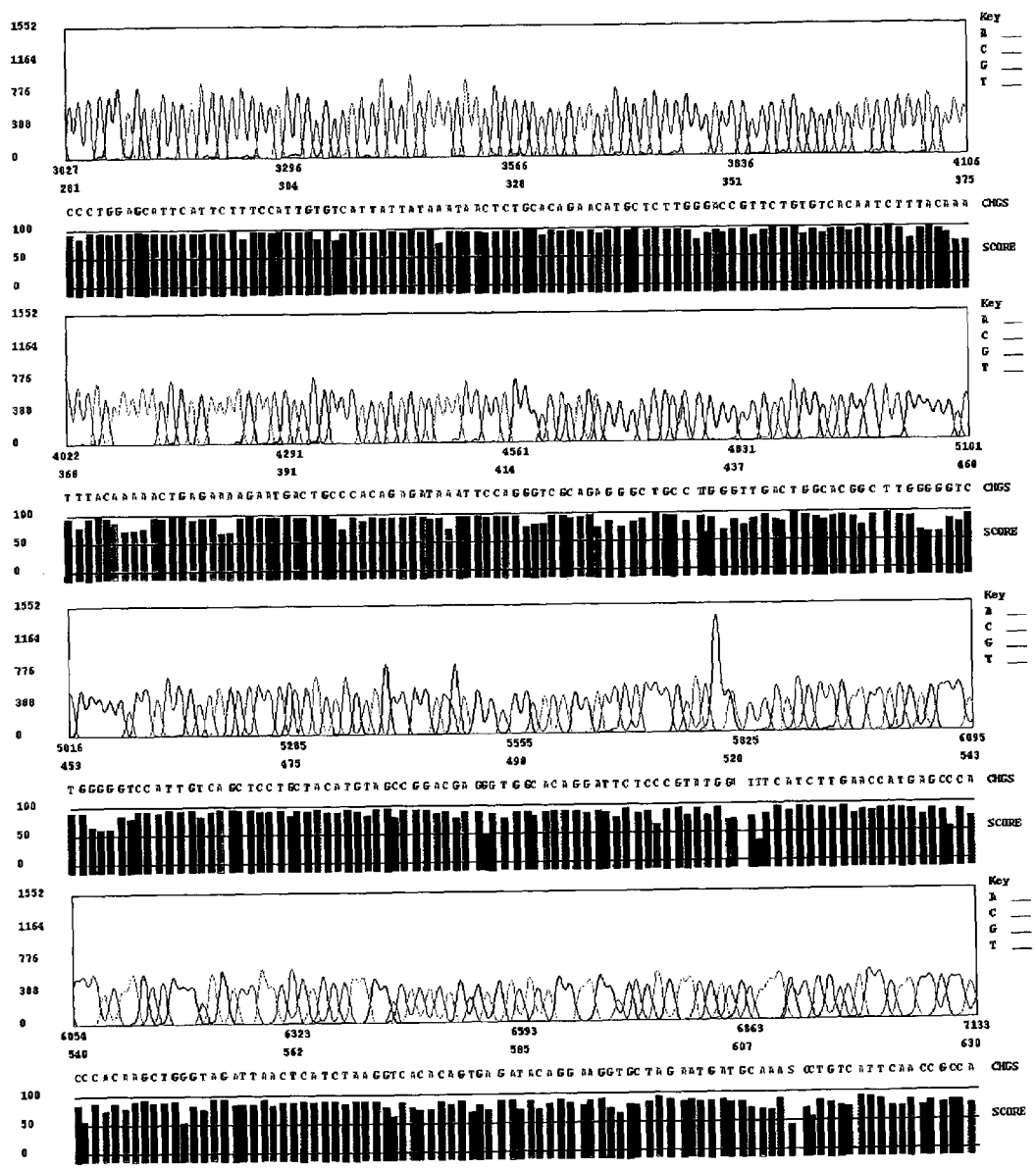
Figure 2A:
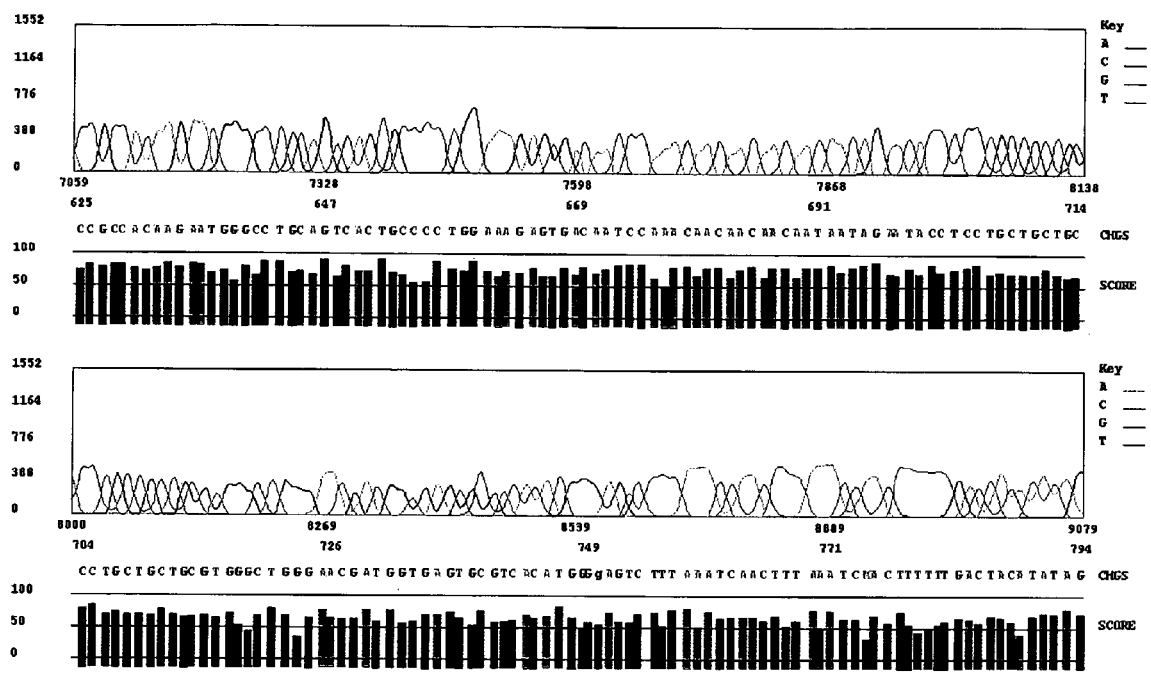
Figure 2B:
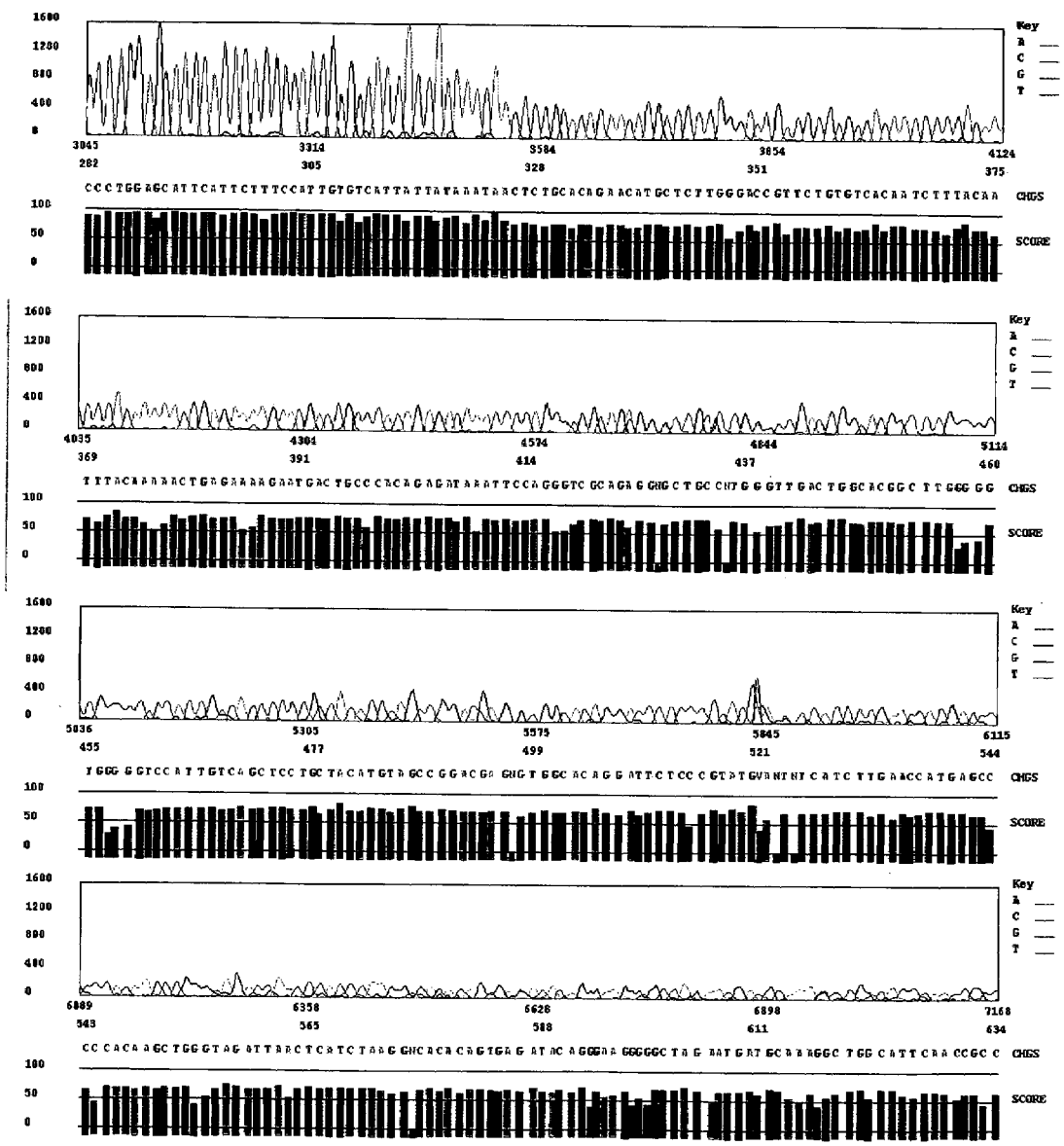
Figure 2B:
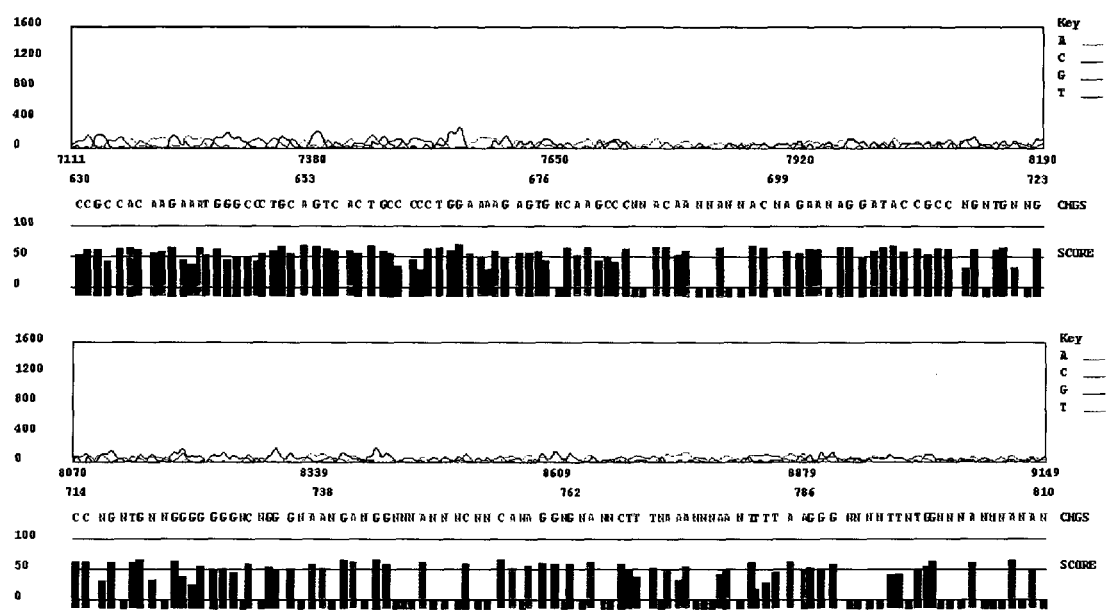

FIGS. 2A and 2B also compare sequencing data generated from a different high GC content template DNA using the same two different sequencing protocols, as above. The quality of the sequence data generated using the method of the invention is excellent throughout most of the picture region of the sequence, while the modified standard sequencing conditions were unable to generate the same quality read length. In this example, the method of the invention was able to generate and additional approximately 100 bases of quality sequence data in comparison to the standard conditions, as determined by the PHRED algorithm (99% confidence level).

Figure 3A:
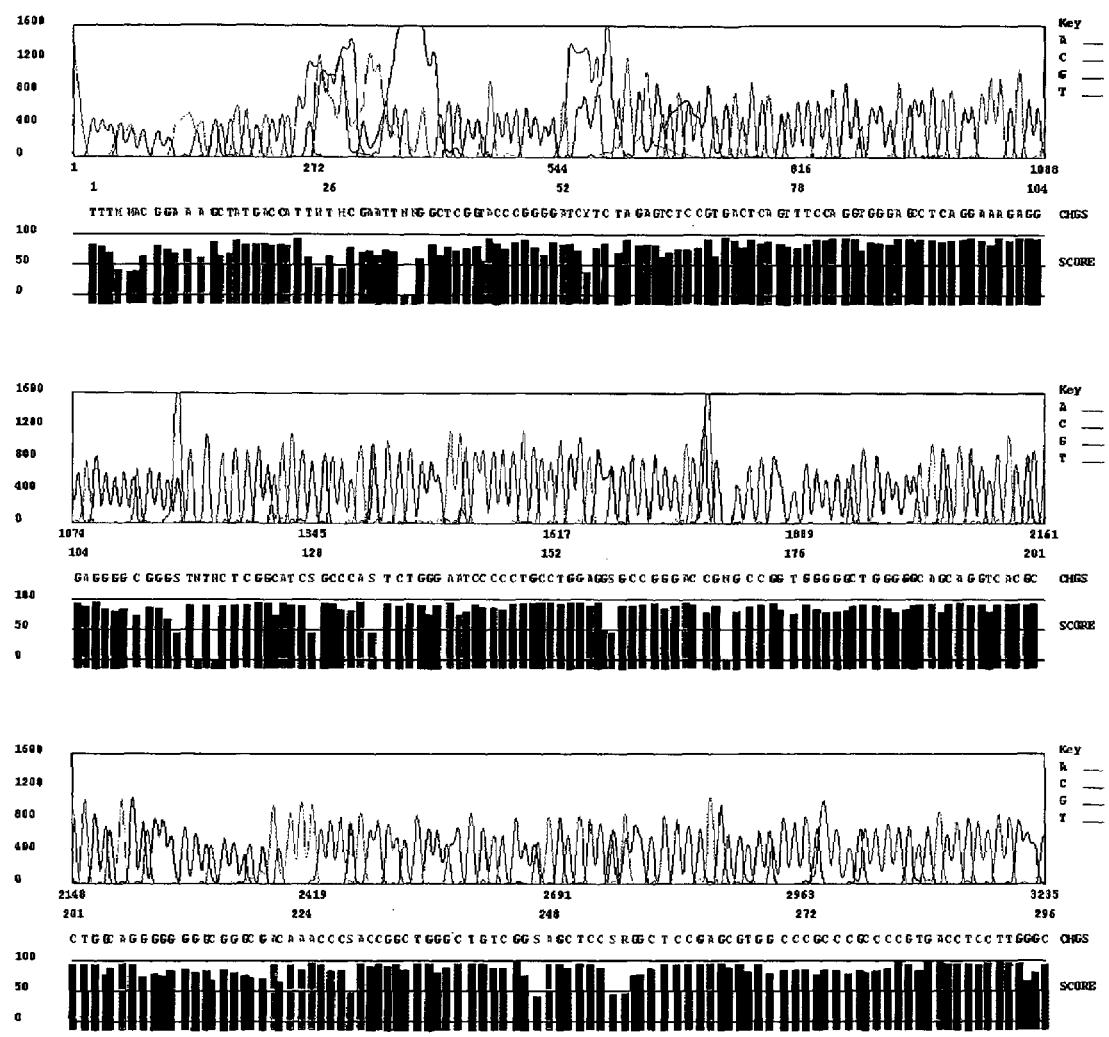
Figure 3A:
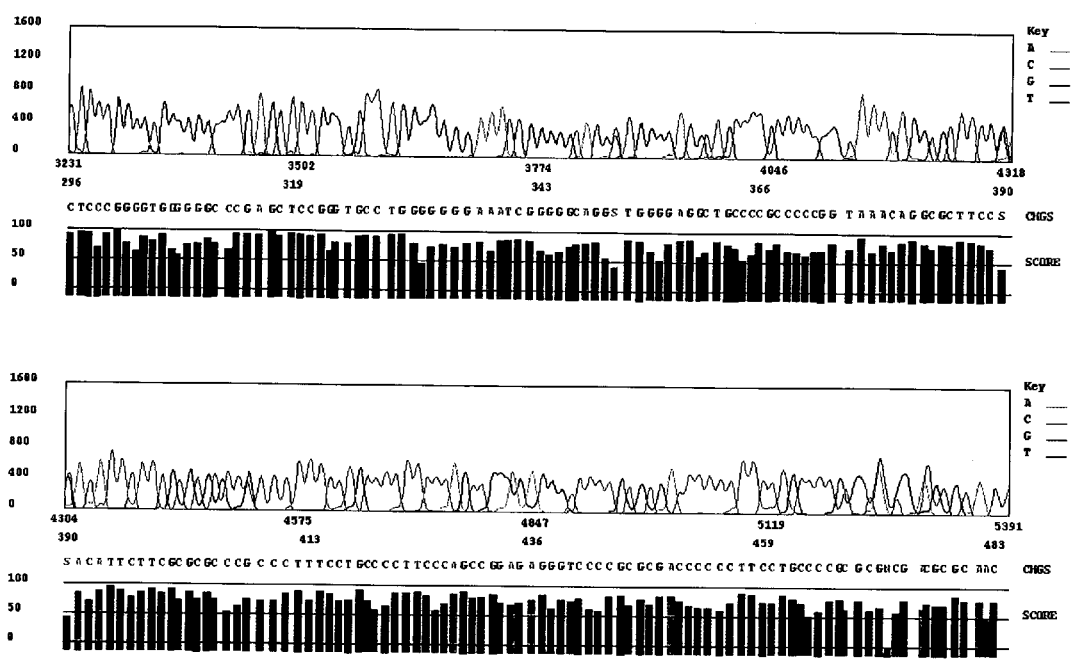
Figure 3B:
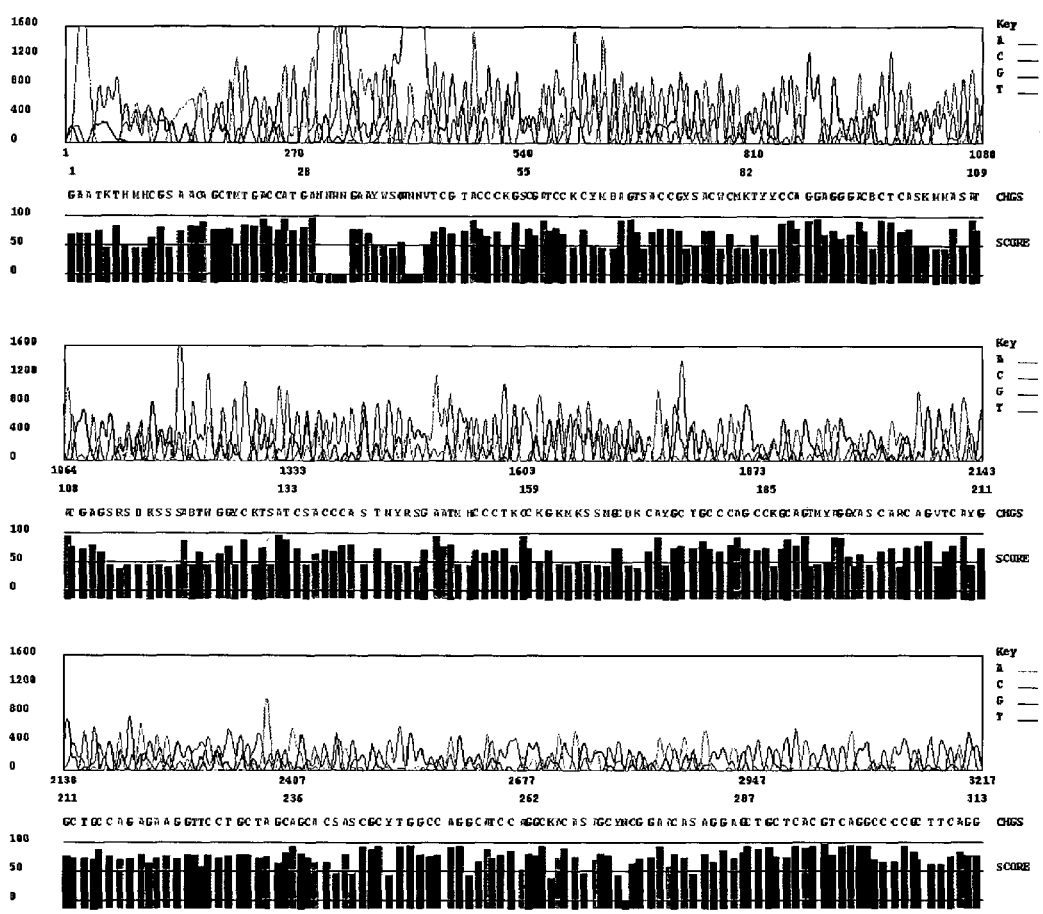
Figure 3B:
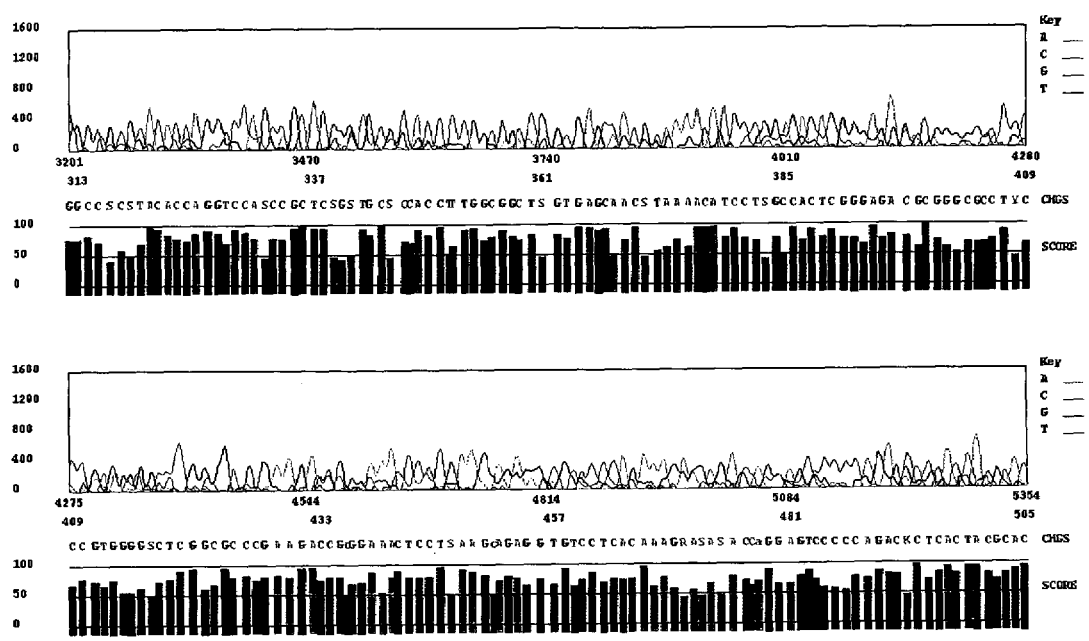

FIGS. 3A and 3B compare sequencing data generated from another high GC content template DNA using the same two different sequencing protocols in an automated dye-terminator cycle sequencer. FIG. 3A shows the sequence data generated using the sequencing method of the invention, i.e., high Td primers and high temperature cycling conditions (see Materials & Methods, supra, for details), and FIG. 4B shows the sequence data generated using standard primers and the high temperature cycling conditions of the invention (see Materials & Methods, supra, for details). The calculated quality base read (using PHRED, 99% confidence) achieved using the method of the invention was 411 base pairs, versus only 116 base pairs using the modified standard sequencing conditions. Indeed, the modified standard conditions resulted in a virtually complete loss of quality data beyond about template nucleotide residue 330. Excellent data, in contrast, was obtained using the method of the invention through about template nucleotide residue 600.

Example 3

CCT Repeat Template Sequencing

Materials and Methods

Automated dye-terminator sequencing of a template DNA containing CCT repeat elements was conducted using both modified standard sequencing conditions and the CCT repeat sequencing method of the invention. An Applied Biosystems model 3700 sequencer was utilized for all sequencing runs.

The reaction mixture was as follows:
- 1.0 µl dGTP BDTv3 terminator mixture, containing polymerase, dNTPs and ddNTPs in a buffer (ABI, Foster City, Calif.)
- 0.0 µl water
- 0.31 µl primer from 6.4 µM stock, yielding a final concentration of 0.48 µl 1.0 µl halfTERM buffer
- 3.0 µl template DNA from 35 ng/ml stock Cycling conditions were as follows:
- Step 1=1 min @ 92° C.
  - ×1 cycle
- Step 2=15 sec @ 92° C.
  - 10 sec @ 54° C.
  - 4 min @ 65° C.
  - ×60 cycles
- Step 3=soak @ 4° C.

Template DNA was prepared using standard techniques and diluted to a final concentration of approximately 33 ng/µl. The primers described in Example 1 were used in the reaction testing the method of the invention, but not in the reaction modified standard sequencing reaction.

Results

The DNA sequencing results obtained using the CCT repeat sequencing method of the invention and modified standard sequencing methodology and conditions on the same template DNA were compared. The results are shown in FIG. 4.

Figure 4A:
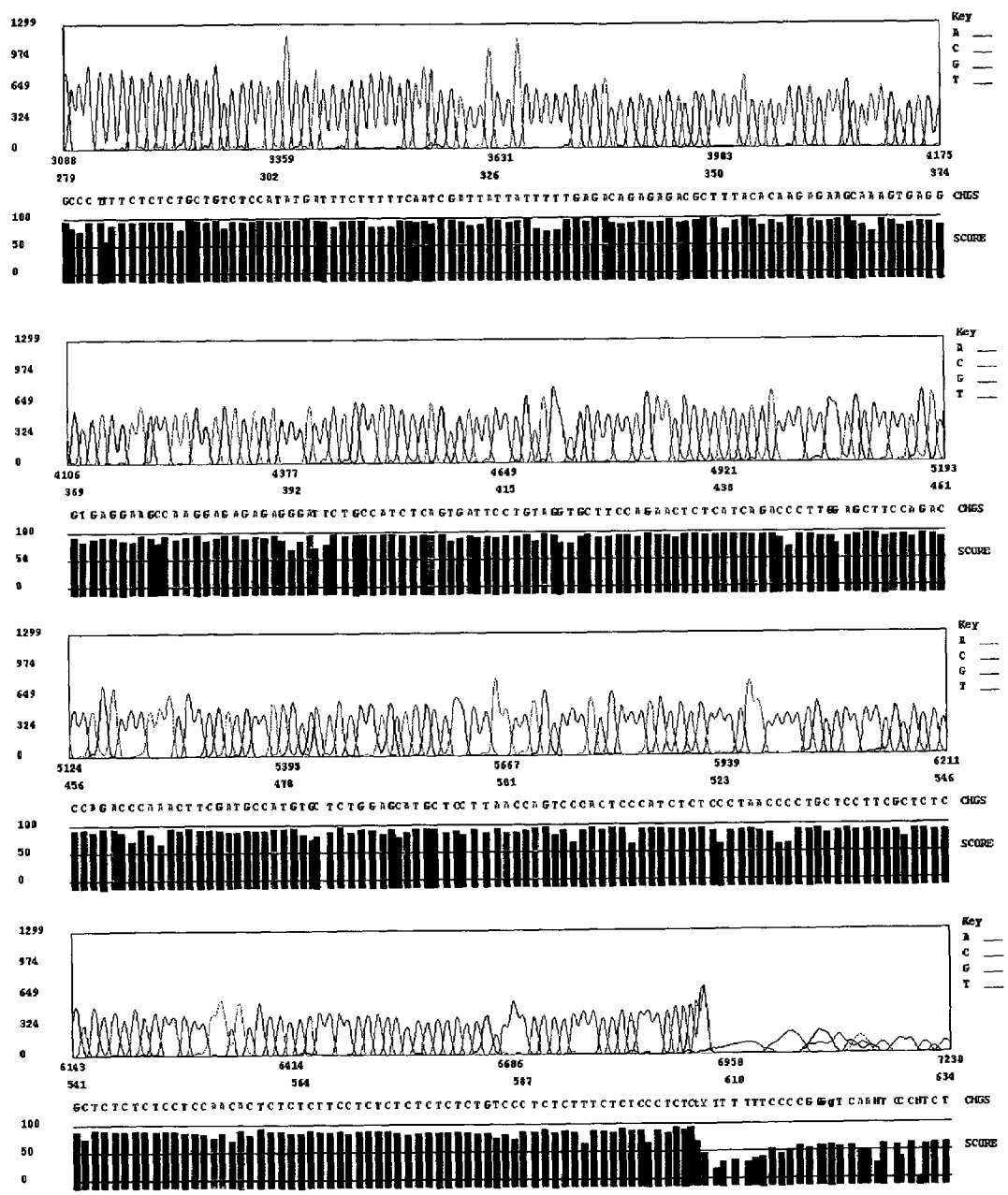
Figure 4B:
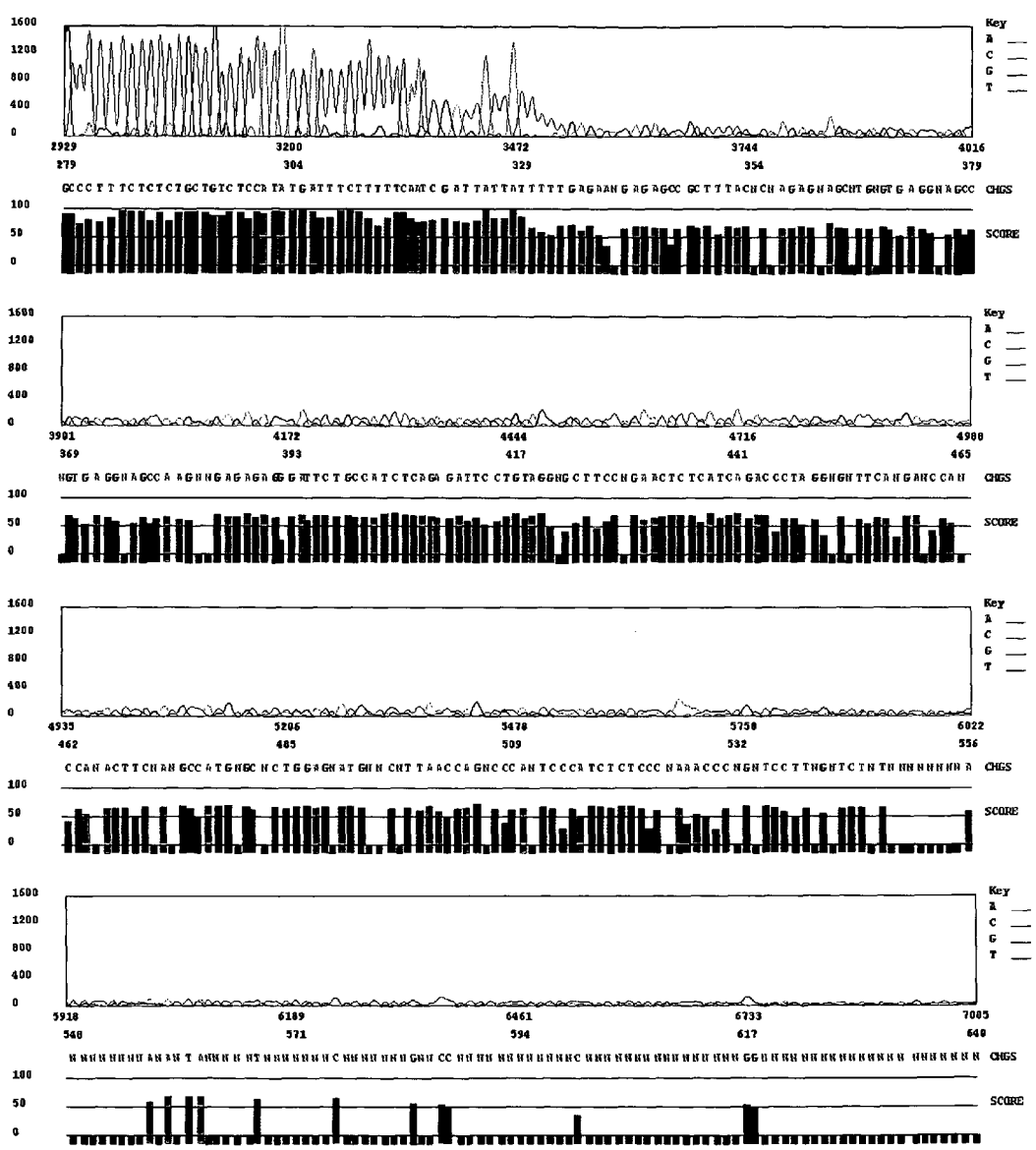

FIGS. 4A and 4B compare sequencing data generated from a CCT repeat-containing template DNA using the above two different sequencing protocols. In this example, the method of the invention was able to generate a quality base read of 586 base pairs, versus only 342 base pairs using the modified standard approach (PHRED algorithm; 99% confidence level).

le;.5qAll publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

SEQUENCE LISTING

<110> Robinson, Donna L.

<120> IMPROVED METHODS FOR SEQUENCINGS GC-RICH AND CCT REPEAT DNA TEMPLATES

<130> S-100,543

<160> 2

<170> Patentin version 3.2

<210> 1
<211> 24
<212 DNA
<213> Artificial
<220>
<223> Artifial Sequence
<400> 1
gctggcaaggc gattaagttg ggta <210> 2
<211> 26
<212> DNA
<213> Artificial
<220>
<223 Artificial Sequence
<400> 2
gttgtgtgga attgtgagcg gataac

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 1
gctgcaaggc gattaagttg ggta                                    24

<210> SEQ ID NO 2
<211> LENGTH: 26
<212> TYPE: DNA
<213> ORGANISM: Artificial Sequence
<220> FEATURE:
<223> OTHER INFORMATION: synthetic oligonucleotide primer

<400> SEQUENCE: 2
gttgtgtgga attgtgagcg gataac                                  26

What is claimed is:

1. A method of fluorescence-based cycle sequencing of a sample DNA, comprising,
   (a) preparing a reaction mixture containing:
      (i) the sample DNA,
      (ii) a primer set complementary to DNA primer sites flanking or interspersed within the sample DNA, wherein the Td of the primers in the primer set are between about 72° C. and 75° C.,
      (iii) a thermostable polymerase,
      (iv) a mixture of dNTPs and fluorescently-labeled ddNTPs, and
      (v) a suitable buffer
   (b), dissociating the sample DNA to create single stranded templates, wherein said dissociation is achieved by heating the sample DNA to between about 92° C. and 95° C. for about 3 minutes;
   (c) annealing the primers to the primer sites, wherein said annealing is achieved at a temperature of between about 65° C. and 67° C. for about 30 seconds;
   (d) extending the annealed primers to generate a series of fluorescently-labeled dideoxynucleic acid fragments, wherein said primer extension is achieved at a temperature of between 75° C. and 78° C. for between about 3 to 4 minutes;
   (e) heating the reaction mixture to between about 92° C. and 95° C. in order to dissociate double stranded DNA;
   (f) repeating the steps c through e for a plurality of cycles; and
   (g) determining the nucleotide sequence of the sample DNA from the series of fluorescently-labeled dideoxynucleic acid fragments present in the reaction mixture.

2. The method according to claim 1, wherein the number of cycles is between about 30 and 50 cycles.

3. The method according to claim 1, wherein the number of cycles is between about 50 and 60 cycles.

4. The method according to claim 1, wherein the number of cycles is between about 60 and 70 cycles.

5. The method according to claim 1, wherein the primers are complementary to a PUC18 vector containing the sample DNA and have the following nucleotide sequences:

```
                                              (SEQ ID NO: 1)
    5' GCT GCA AGG CGA TTA AGT TGG GTA 3'

(SEQ ID NO: 2)
    5' GTT GTG TGG AAT TGT GAG CGG ATA AC 3'
```

6. The method according to claim 5, wherein primer annealing is achieved at 67° C. for 30 seconds, and primer extension is achieved at 75° C. for 4 minutes.

7. The method according to claim 1, wherein the thermostable DNA polymerase is a Taq polymerase.

8. The method according to claim 1, wherein the Taq polymerase contains a F667Y point mutation.

9. A method of sequencing a GC-rich DNA sample on an automated fluorescence-based cycle sequencer, comprising
   (a) providing primers having a Td of between about 73° C. and 74° C. in a dye-terminator sequencing reaction comprising the DNA sample, a Taq polymerase and dNTPs and fluorescently-labeled ddNTPs, in a suitable buffer, under substantially the following cycle conditions:
   Step 1=3 min @ 92° C.
   ×1 cycle
   Step 2=30 sec @ 92° C.
   30 sec @ 67° C.
   4 min @ 75° C.
   ×60 cycles
   Step 3=soak @ 4° C.
   (b) determining the nucleotide sequence of the DNA sample.

10. A method of sequencing a DNA sample containing CCT repeats on an automated fluorescence-based cycle sequencer, comprising (a) providing primers having a Td of between about 57° C. and 75° C. in a dye-terminator sequencing reaction comprising the DNA sample, a Taq polymerase and dNTPs and fluorescently-labeled ddNTPs, in a suitable buffer, under substantially the following cycle conditions:

Step 1=1 min @ 92° C.
  ×1 cycle

Step 2=15 sec @ 92° C.
  10 sec @ 54° C.
  4 min @ 65° C.
  ×60 cycles

Step 3 soak @ 4° C.

(b) determining he nucleotide sequence of the DNA sample.

* * * * *